(12) United States Patent
Appavoo et al.

(10) Patent No.: US 9,756,855 B2
(45) Date of Patent: Sep. 12, 2017

(54) ANTIMICROBIAL PARTICLE AND COMPOSITIONS THEREOF

(71) Applicant: Conopco, Inc., Englewood Cliffs, NJ (US)

(72) Inventors: Shanthi Appavoo, Chennai (IN); Arpita Bhattacharya, Jabalpur (IN); Sudipta Ghosh Dastidar, Bangalore (IN); Maya Treesa Saji, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/914,415

(22) PCT Filed: Sep. 2, 2014

(86) PCT No.: PCT/EP2014/068592
§ 371 (c)(1),
(2) Date: Feb. 25, 2016

(87) PCT Pub. No.: WO2015/032739
PCT Pub. Date: Mar. 12, 2015

(65) Prior Publication Data
US 2016/0205928 A1 Jul. 21, 2016

(30) Foreign Application Priority Data
Sep. 5, 2013 (EP) .................... 13183091

(51) Int. Cl.
| | | |
|---|---|---|
| *A01N 31/08* | (2006.01) |
| *A01N 31/04* | (2006.01) |
| *A61K 8/02* | (2006.01) |
| *A61L 2/18* | (2006.01) |
| *A61L 9/013* | (2006.01) |
| *A61K 8/26* | (2006.01) |
| *A61K 8/34* | (2006.01) |
| *A01N 25/26* | (2006.01) |
| *A61Q 17/00* | (2006.01) |
| *A61Q 19/10* | (2006.01) |

(52) U.S. Cl.
CPC ............ *A01N 31/08* (2013.01); *A01N 25/26* (2013.01); *A01N 31/04* (2013.01); *A61K 8/0279* (2013.01); *A61K 8/26* (2013.01); *A61K 8/34* (2013.01); *A61K 8/347* (2013.01); *A61L 2/18* (2013.01); *A61L 9/013* (2013.01); *A61K 2800/621* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 5,010,109 A | 4/1991 | Inoi | |
| 2006/0069002 A1* | 3/2006 | Song ................ | C11D 3/06 510/220 |
| 2006/0115440 A1* | 6/2006 | Arata ................ | A61K 8/19 424/65 |
| 2009/0199314 A1 | 8/2009 | Gaudillat | |
| 2011/0223114 A1* | 9/2011 | Chakrabortty ......... | A01N 31/04 424/43 |

FOREIGN PATENT DOCUMENTS

| | | |
|---|---|---|
| EP | 2140853 | 1/2010 |
| WO | WO9428107 | 12/1994 |
| WO | WO2010046238 | 4/2010 |

OTHER PUBLICATIONS

Search Report and Written Opinion in EP13183091, Feb. 24, 2014.
Search Report and Written Opinion in PCTEP201406859, Nov. 25, 2014.

* cited by examiner

*Primary Examiner* — Robert A Wax
*Assistant Examiner* — Quanglong Truong
(74) *Attorney, Agent, or Firm* — Ronald A. Koatz

(57) ABSTRACT

The invention relates to an antimicrobial particle and to a composition for use in personal or home care products comprising the same. The invention also relates to a process for preparing the antimicrobial particle. The antimicrobial particle comprises thymol and terpineol incorporated in a cage-forming inorganic silicate or aluminosilicate particle which is coated with a coating material selected from a water soluble alkali or alkaline earth metal salt.

11 Claims, No Drawings

ANTIMICROBIAL PARTICLE AND COMPOSITIONS THEREOF

FIELD OF THE INVENTION

The invention relates to an antimicrobial particle and to a composition for use in personal or home care products comprising the same.

BACKGROUND OF THE INVENTION

Traditionally, antimicrobial compounds are included in personal care or home care compositions to achieve disinfection of surfaces. When such compositions are of the wash-off type, the anti-microbial active does not have sufficient time available during the short period of time over which the washing is carried out, to ensure the desired activity. Further, the amount of anti-microbial active left on the surface after it has been washed off is low and therefore further possible antimicrobial efficacy is low.

The present applicant has disclosed in WO20100046238 that a composition comprising terpineol and thymol provides for enhanced germ reduction in fast acting time frames, in many cases in as low as 15 seconds after application of the composition on the desired surface.

One of the disadvantages of incorporating these actives especially thymol in sufficient quantities to ensure the desired fast acting antimicrobial activity is that the concentration at which thymol is used causes a strong medicinal odour to the composition which may not be liked by some people. Thus, there is a need to either reduce the concentration of this active or ensure that the odour impact is minimised.

The present inventors have been able to ensure the antimicrobial efficacy of these actives from wash-off compositions as well as enable it in leave-on compositions by incorporating these actives in a caged inorganic structure and providing sufficient stability during storage and thereby enhanced efficacy in use, by efficient coating of the particles using select materials. The invention thus ensures use of lower amount of antimicrobial actives, reduced issues like off-odour and enhanced antimicrobial efficacy. This invention, therefore has applications in products like soaps, detergents, shampoos, hand-wash products, hard-surface cleaning products, oral care products like toothpaste and toothpowders, and in leave on products like skin creams and lotions, hair gels, and sprays and products for use in household care applications.

Antimicrobial actives incorporated in zeolites have been reported. U.S. Pat. No. 5,010,109 (Chisso, 1991) discloses a novel antimicrobial, aromatic and deodorizing agent, a composition and a method of reducing microbial concentration or inhibiting microbial growth using the composition, which composition comprises a zeolite or porous glass carrier and a saturated monoterpene hydroperoxide as an active ingredient, the monoterpene hydroperoxide preferably selected from pinane hydroperoxide, thujane hydroperoxide, carane hydroperoxide, bornane hydroperoxide, paramenthane hydroperoxide, metamenthane hydroperoxide, and mixtures.

The published documents do not exhibit the enhanced delivery of the actives provided by the present invention. It is thus an object of the present invention to provide enhanced antimicrobial efficacy of the fast acting actives thymol and terpineol while ensuring that off-odours are masked during storage and use. The advantage of the present invention over published knowledge like in U.S. Pat. No. 5,010,109 is that antimicrobial actives thymol and terpineol which interact synergistically to provide antimicrobial activity are suitably encapsulated in a caged inorganic particle and suitably coated so as to minimize off odour when formulated in a personal care or cleansing composition while ensuring the desired fast antimicrobial activity when in use, by way of enhanced deposition on to the substrate.

SUMMARY OF THE INVENTION

According to the first aspect of the present invention there is provided an antimicrobial particle comprising thymol and terpineol incorporated in a cage-forming inorganic silicate or aluminosilicate particle, the cage-forming inorganic silicate or aluminosilicate particle is coated with a coating material selected from a water soluble alkali or alkaline earth metal salt.

According to a preferred aspect of the present invention there is provided a composition for care or cleansing of the external surface of a human or animal body or the external surface of an inanimate object comprising 0.5 to 20% of an antimicrobial particle of the first aspect of the present invention.

According to another aspect of the present invention there is provided a process to prepare the antimicrobial particle of the first aspect comprising the steps of
(i) Mixing the cage-forming inorganic silicate or aluminosilicate particle in an aqueous suspension of thymol and terpineol;
(ii) filtering and rinsing the particle of step (i) in water;
(iii) mixing the particle of step (ii) in an aqueous solution of the coating material; and
(iv) filtering and drying particle of step (iii) to obtain the desired antimicrobial particle.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

By a composition for external care or cleansing of the external surface of a human or animal body means a composition in the form of a leave-on or wash-off format meant for cleaning or disinfecting topical areas e.g. skin and/or hair of mammals, especially humans. Such a composition includes any product applied to a human body for also improving appearance, cleansing, odor control or general aesthetics. It is preferably a rinse off product. The composition of the present invention may be in the form of a liquid, lotion, cream, foam or gel, or toner, or applied with an implement or via a face mask, pad or patch. "Skin" as used herein is meant to include skin on the face and body (e.g., neck, chest, back, arms, underarms, hands, legs, buttocks and scalp). The composition of the invention is also of relevance to applications on any other keratinous substrates of the human body other than skin e.g. hair or oral cavity where products may be formulated with specific aim of providing disinfection and cleaning.

By a composition for care or cleansing of the external surface of an inanimate object means a composition in the form of a leave-on or rinse-off format meant for cleaning or disinfecting surfaces in homes or out-of-homes. These hard surfaces include external surfaces like floors, walls, windows, doors, furniture, and table tops in various indoor and outdoor locations. Toilets and bathrooms are other places where germs proliferate and disinfection and cleaning compositions of the present invention may be used. Other types of hard surfaces that are cleaned by such compositions include utensils and other articles found in households, offices and other public places.

An antimicrobial particle of the present invention comprises two essential oil actives: thymol and terpineol.

Thymol

The structure of thymol is given below:

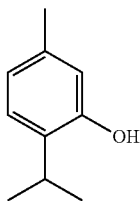

Thymol may be added to the particle in purified form. Alternatively, thyme oil or thyme extract comprising thymol may be added to the particle, while ensuring that thymol is present in the desired concentration in the particle of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide,* and *Thymus citriodorus.*

Terpineol

The structure of a terpineol compound is given below:

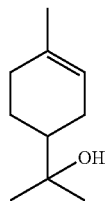

The terpineol is preferably selected from alpha-terpineol, beta-terpineol, gamma-terpineol or mixtures thereof. It is particularly preferred that the terpineol is alpha-terpineol. Terpineol may be added to the antimicrobial particle in purified form. Alternatively pine oil comprising terpineol may be added to the antimicrobial composition while ensuring that terpineol is present in the desired concentration in the antimicrobial particle of the present invention.

The antimicrobial particle preferably comprises 0.1 to 5%, more preferably 1 to 4%, more preferably 1 to 3%, by weight terpineol. The antimicrobial particle of the invention preferably comprises 0.1 to 10%, preferably 1 to 5%, more preferably 1 to 4%, by weight thymol. The total amount of essential oil actives thymol and terpineol is preferably from 0.5 to 10% by weight of the antimicrobial particle.

The composition may optionally comprise additional essential oil actives preferably eugenol, geraniol or a mixture thereof.

The essential oil actives terpineol and thymol are incorporated in a cage-forming inorganic silicate or aluminosilicate particle.

Aluminosilicate particles are minerals composed of aluminium, silicon, and oxygen, and their countercations. They are a major component of kaolinite and other clay minerals. Andalusite, kyanite, and sillimanite are naturally occurring aluminosilicate minerals that have the composition $Al_2SiO_5$. Hydrated aluminosilicate minerals are referred to as zeolites and are porous structures that are naturally occurring materials.

The aluminosilicate is preferably a zeolite. Zeolites are tectosilicates consisting of interlocking $SiO_4$ and $AlO_4$ tetrahedrons, which share oxygen atoms. Whilst the silicate groups are neutral, the alumina groups carry a negative charge, which has to be balanced by positively charged ions. They have large vacant spaces or cages in their structure that allow space for large cations such as sodium, potassium, barium and calcium and even relatively large molecules and cation groups such as water, ammonia, carbonate ions and nitrate ions. Their general formula is $Mx/n[(AlO2) \times (SiO2)y].mH2O$ where cations 'M' of valence 'n' neutralize the negative charges on the aluminosilicate framework. The examples of a few zeolites are as follows:

Zeolite 4A and 5A have the ratio of Si to Al as 1 and their cavity is made up of 8 member rings of Silica and Alumina tetrahedron. Their pores are 4A° for zeolite 4A and 5A° for zeolite 5A.

Zeolite 13X has the Si to Al ratio of 2 to 3 and the cavity is made up of 12 member rings of Silica and Alumina tetrahedron. The pore size is 10A°

Of the various types of zeolites, the preferred zeolite is a zeolite 4A, a zeolite 5A or a zeolite 13X. The particle comprises 80 to 98% of the cage-forming inorganic silicate or aluminosilicate by weight of the particle, while the essential oil actives and a coating material preferably make up the balance of the particle. Preferably the cage-forming inorganic silicate or aluminosilicate makes up 90 to 95% by weight of the particle. The particle preferably has a size in the range of 0.5 to 20 µm, more preferably in the range of 1 to 5 µm.

The cage-forming inorganic silicate needs to be coated with a coating material selected from a water soluble alkali or alkaline earth metal salt. The coating material provides advantages of a judicial balance between minimizing the release of antimicrobial agent during processing while ensuring better dispersability of the particle.

Of these two types, the metal salt is more preferred. Preferred water soluble alkali or alkaline earth metal salts are chloride, sulphate, sulphite, citrate, carbonate or bicarbonate of sodium, potassium, magnesium, or calcium. Most preferred water soluble metal salts are chloride, sulphate, sulphite, citrate, carbonate or bicarbonate of sodium, potassium, magnesium, or calcium.

The coating material is preferably present in 1 to 19%, more preferably 2 to 10% by weight of the particle.

According to another aspect of the present invention there is provided a composition for care or cleansing of the external surface of a human or animal body or the external surface of an inanimate object comprising 0.5 to 20% of an antimicrobial particle of the invention by weight of the composition. The composition of the invention is preferably used for care or cleansing of external surface of human body or for cleaning or disinfection of surfaces in homes or for cleaning fabric. The composition is preferably used for cleansing in which case the composition is a wash-off product. The external surface of the human body includes skin, hair, scalp, the axilia or the oral cavity.

The composition comprising the antimicrobial particle preferably comprises a carrier. The carrier is selected from water, oil, solvent, inorganic particulate material, starch and mixtures thereof. The carrier is preferably from 0.1 to 99.5% by weight of the composition. The composition may be in form of a solid, liquid, gel, paste or soft solid and the carrier may be selected by a person skilled in the art depending on the format of the composition. When water is present, it is preferably present in at least 1%, more preferably at least 2%, further more preferably at least 5% by weight of the composition. When water is the carrier, a preferred liquid composition comprises 10 to 98% by weight water, and 1 to 30% by weight surfactant, in addition to the essential ingredient of the inventive composition. When water is the carrier, a preferred solid composition comprises 5 to 30% by weight water, and 30 to 90% by weight surfactant, in addition to the essential ingredient of the inventive composition.

In most of the envisaged applications like personal care/washing, oral care and hard surface cleaning, the antimicrobial composition may be formulated in an aqueous base (water being carrier) e.g. products in gel format or in purely oil/solvent base e.g. products in anhydrous stick form or propellant containing products. However, most preferred product format has an emulsion base (water and oil being the carrier) e.g. products in liquid, solid, lotion or semisolid form for hand wash, face wash, body wash, or shaving applications; toothpaste/dentifrices for oral care applications or products for hard surface cleaning in bars or liquids form.

The composition preferably comprises 1 to 80% surfactant by weight of the composition.

In general, the surfactants may be chosen from the surfactants described in well known textbooks like "Surface Active Agents" Vol. 1, by Schwartz & Perry, Interscience 1949, Vol. 2 by Schwartz, Perry & Berch, Interscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981. Any type of surfactant, i.e. anionic, cationic, nonionic, zwitterionic or amphoteric can be used.

A particularly preferred surfactant is soap. Soap is a suitable surfactant for personal washing applications of the antimicrobial composition of the invention. The soap is preferably C8-C24 soap, more preferably C10-C20 soap and most preferably C12-C16 soap. The soap may or may not have one or more carbon-carbon double bond or triple bond. The cation of the soap can be alkali metal, alkaline earth metal or ammonium. Preferably, the cation of the soap is selected from sodium, potassium or ammonium. More preferably the cation of the soap is sodium or potassium.

The composition of the invention is useful in hard surface cleaning applications. In such applications preferred surfactants are nonionic surfactants, such as C8-C22, preferably C8-C16 fatty alcohol ethoxylates, comprising between 1 and 8 ethylene oxide groups when the product is in the liquid form. When the product is in the solid form for hard surface cleaning applications surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Suitable surfactant concentrations in liquid forms of hard surface cleaning application are generally from about from 0.5 to 10%, preferably from 1 to 5% by weight of the composition. In solid compositions, surfactant is preferably present in 5 to 40%, preferably from 10 to 30% by weight of the composition.

The composition of the invention is useful in oral care compositions e.g. in a dentifrice/toothpaste or oral rinse product. In such applications, preferred surfactants are anionic, nonionic or amphoteric in nature, preferably anionic or amphoteric. Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10~C18 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, in a highly preferred aspect, the compositions may include one or more of soap, alkyl sulphate or linear alkyl benzene sulphonate as the surfactants.

The composition of the invention is especially useful in providing fast antimicrobial activity in a wash off process where the contact time of the antimicrobial actives with the surface is low, i.e. of the order of less than 5 minutes, preferably less than 2 minutes, further more preferably less than a minute and in many cases less than 30 seconds or even less than 15 seconds.

The composition may further comprise various additional ingredients known to a person skilled in the art. Such additional ingredients include but are not limited to: perfumes, pigments, preservative, emollients, sunscreens, emulsifiers, gelling agents, or thickening agents.

The composition of the invention preferably comprises very low amounts of harsh antimicrobial actives e.g. those containing chlorine or other halogens or low molecular weight (C2 to C4) alcohol. These harsh actives, if present is low i.e less than 1%, preferably less than 0.5%, more preferably less than 0.1% by weight of the composition, and optimally they are absent in the composition.

According to another aspect of the present invention there is provided a method of disinfecting a surface comprising the steps of (a) applying a composition of the invention on to the surface; and (b) rinsing the surface with a suitable solvent.

The solvent for rinsing the surface is preferably water but could also be a mixture of water and alcohol. The word rinsing herein includes the act of wiping the surface with a suitable wipe. Thus the surface e.g hand, face, body, oral cavity or any hard surface e.g. a utensil is first contacted with the composition of the invention. It is then rinsed preferably with sufficient amounts of water after a pre-determined period of time to remove any visible or sensory reside of the composition. Alternately an alcohol wipe or a water/alcohol impregnated wipe may be used to wipe the surface to be visibly free of the anti-microbial composition. The step of rinsing the substrate is preferably carried out less than 5 minutes, preferably less than 2 minutes, further more preferably less than a minute and in many cases less than 30 seconds or even less than 15 seconds after the step of applying the composition on the substrate.

According to one aspect, the invention provides for non-therapeutic benefits.

According to yet another aspect of the invention there is provided use of the composition of the invention for enhanced antimicrobial activity by way of better deposition of the active on to the desired surface.

According to yet another aspect of the present invention there is provided a process to prepare the antimicrobial particle of the present invention comprising the steps of
(i) mixing the cage-forming inorganic silicate or aluminosilicate particle in an aqueous suspension of thymol and terpineol;
(ii) filtering and rinsing the particle of step (i) in water;
(iii) mixing the particle of step (ii) in an aqueous solution of the coating material; and
(iv) filtering and drying particle of step (iii) to obtain the desired antimicrobial particle.

A highly preferred process to prepare the antimicrobial particle of the invention is as follows. Zeolite 4A (2 gram) is taken in about 100 ml of a mixture of de-ionized water in ethanol (95:5 mixture). Two grams of a mixture of terpineol (about 1.42 gram) and thymol (about 0.58 gram) is then added slowly while stirring the mixture for about 8 hours. The mixture is then filtered and rinsed well with water. The powder is then mixed in 100 ml of a 20% sodium carbonate solution. The powder is then filtered and then dried in a hot air oven at 40° C. The powder is then coated using the following preferred procedure:
1 g of the zeolite containing the thymol and terpineol is taken in a 50 ml Tarson Tube with 10 ml of a solution of the coating material. Typically the coating material is prepared as a 10% solution in the case of inorganic salts or a 0.5% solution in the case of polymers. The mixture is then shaken well for about 3 to 4 minutes in a vortex mixer at low speed and then centrifuged. The supernatant is discarded and the particles are dried.

According to the present invention there is provided the use of an antimicrobial particle according to the present invention in a composition for care or cleansing of the external surface of a human or animal body or the external surface of an inanimate object, to improve the deposition of the active on to the desired surface.

The external surface of the human body preferably includes skin, hair, scalp, the axilia or the oral cavity.

The antimicrobial particle as mentioned for the use comprising thymol and terpineol incorporated in a cage-forming silicate or aluminosilicate particle, whereby said cage-forming inorganic silicate or aluminosilicate particle is coated with a coating material selected from a water soluble alkali or alkaline earth metal salt. The preferred cage-forming inorganic aluminosilicate is a zeolite. The preferred zeolite may is a zeolite 4A, a zeolite 5A or a zeolite 13X. The antimicrobial particle as mentioned for the use preferably comprising 80 to 98% cage-forming inorganic silicate or aluminosilicate by weight of the antimicrobial particle. The antimicrobial particle as used preferably comprising 0.1 to 5%, more preferably 1 to 4% and further more preferably 1 to 3% terpineol and 0.1 to 10%, preferably 1 to 5%, most preferably 1 to 4% thymol by weight of the particle.

According to the present invention there is also provided the use of a composition according to the present invention for enhanced antimicrobial activity. The details about the composition are disclosed herein in the previous paragraphs. Thus, any preferred feature of the composition according to the invention is also preferred in this use of the composition. Enhanced antimicrobial activity preferably involves faster reduction of antimicrobial count. Preferably, the use of the composition is non-therapeutic use.

The invention will now be illustrated with the help of the following non-limiting examples.

EXAMPLES

Examples A to D and Example 1: Antibacterial Activity of Antimicrobial Particle as Per the Invention as Compared to Control Using *S. Aureus* as the Micro-Organism Thymol and terpineol were encapsulated in zeolite 4A particles using the following procedure. Two gram of zeolite 4A were taken in 100 ml of de-ionised water. 0.28 gram of thymol and 0.71 gram of terpineol were added slowly to the suspension with stirring. The stirring was continued for 8 hours. The mixture was thereafter filtered and rinsed well with water. The powder was then mixed with a 20% solution of sodium carbonate in water to ensure coating of the particle with the soda. The solution was then filtered and dried in a hot air oven at 40° C.

Example A to D, 1: Activity Against *S. aureus*

Example—A: *S. aureus* control
Example—B: Zeolite 4A with no thymol or terpineol encapsulated
Example—C: Zeolite 4A with no thymol or terpineol encapsulated but coated with soda
Example—D: Thymol (0.1%)+terpineol (0.25%) as such, without zeolite
Example—1: Thymol (0.2±0.01%) and terpineol (0.15±0.04%) encapsulated in zeolite 4A and coated with soda (Quantified using GC)

Examples E to G and Example—2: Experiments were Conducted with *S. mutans* as the Microorganism for the Following Samples Example—E: *S. mutans* control
Example—F: Zeolite 4A with no thymol or terpineol encapsulated
Example—G: Thymol (0.1%)+terpineol (0.25%) as such, without zeolite
Example—2: Thymol (0.2±0.01%) and terpineol (0.15±0.04%) encapsulated in zeolite 4a further coated with soda The antibacterial activity of all the above samples were tested using the following procedure:
The test bacteria was grown overnight at 37° C. on TSA plate. The grown culture colonies were resuspended in 0.8% saline solution. The culture cell density was adjusted to get the final count of $10^8$ cfu/ml. 9 ml of the test solution was taken in a sterile sample container and 1 ml of the test culture was added. After the specified contact time, 1 ml of the above mixture was immediately neutralized in 9 ml D/E broth as commonly used in the art. This was again serially diluted in D/E broth and plated on TSA (Tryptic Soy Agar) in duplicates. In case of the control, 1 ml of test culture was added to 9 ml of saline and was serially diluted and plated on TSA. After solidification, the plates were incubated at 37° C. for 48 hrs and the residual colonies were counted. All the antimicrobial experiments were performed under aseptic condition under laminar air flow and all the agar media and D/E dilution tubes were autoclaved (15 psig, 121° C., 15-20 minutes) before use.

The data (in terms of log reduction) is summarized in Table—1 below:

TABLE 1

| Example | Sample | Log reduction |
|---|---|---|
| A | *S. aureus* control | No reduction |
| B | Zeolite 4A control | No reduction |
| C | Zeolite 4A coated with soda | No reduction |
| D | 0.1% thymol + 0.25% terpineol | 0.3 |
| 1 | Thymol (0.2 ± 0.01%) and terpineol (0.15 ± 0.04%) encapsulated in Zeolite 4A further coated with soda. | 7.2 |
| E | *S. mutans* control | No reduction |
| F | Zeolite 4A control | No reduction |
| G | 0.1% thymol + 0.25% terpineol | 0.4 |
| 2 | Thymol (0.2 ± 0.01%) and terpineol (0.15 ± 0.04%) encapsulated in Zeolite 4A further coated with soda. | 7.2 |

The data in Table—1 above indicates that thymol and terpineol when encapsulated in Zeolite as per the invention provides for vastly improved antimicrobial activity, as compared to control samples.

Example H and 3: Deposition Study

The efficiency of deposition of thymol and terpineol through use of a particle as per the invention when incorporated in a soap was compared to use of terpineol and thymol incorporated, as such, in a soap. The procedure used was as follows:

Example H: An 8% solution of a market sample of Lifebuoy soap bar was prepared. To this solution was added thymol and terpineol such that the weight percent of thymol was 0.47% and terpineol was 0.80%.

Example 3: An 8% solution of a market sample of Lifebuoy soap bar was prepared. To this solution was added 300 mg of antimicrobial particles such that the amount of thymol and terpineol were the same as for Example H The amount of deposition was measured using the following procedure.

Six slides of Transpore tape used for one set of experiments. 500 µl of the above solution was applied on each of the slides and left for one minute. The product was then rinsed off using a stream of water. The amount of thymol and terpineol deposited from all six slides was extracted using 10 ml of methanol. This solution was injected into a GC to quantify the amount of actives that were deposited. The data for each of the samples for both terpineol and thymol is summarized in Table—2.

TABLE 2

| Examples | Sample | Amount in ng per $cm^2$. |
|---|---|---|
| H | Terpineol | 200.6 |
| 3 | Terpineol | 422.8 |
| H | Thymol | 183.5 |
| 3 | Thymol | 498.3 |

The data in Table—2 indicates that samples as per the invention (Example 3) provide for vastly superior deposition of the actives as compared to conventional way of adding actives to soap.

The invention claimed is:

1. An antimicrobial particle comprising thymol and terpineol incorporated and encapsulated in a cage-forming inorganic silicate or aluminosilicate particle, whereby said caged inorganic silicate or aluminosilicate particle is coated with a coating material selected from a water soluble alkali or alkaline earth metal salt:
   wherein preparation of said antimicrobial particle comprises the following steps:
   (i) mixing said caged inorganic silicate or aluminosilicate particle in an aqueous suspension of thymol and terpineol;
   (ii) filtering and rinsing said particle of step (i) in water;
   (iii) mixing the particle of step (ii) in an aqueous solution of said coating material; and
   (iv) filtering and drying particle of step (iii) to obtain the desired antimicrobial particle.

2. An antimicrobial particle as claimed in claim 1 wherein said cage-forming inorganic aluminosilicate is a zeolite.

3. An antimicrobial particle as claimed in claim 2 wherein said zeolite is a zeolite 4A, a zeolite 5A or a zeolite 13X.

4. An antimicrobial particle as claimed in claim 1 wherein said salt is selected from chloride, sulphate, sulphite, citrate, carbonate or bicarbonate of sodium, potassium, magnesium, or calcium.

5. An antimicrobial particle as claimed in claim 1 comprising 80 to 98% cage-forming inorganic silicate or aluminosilicate by weight of the antimicrobial particle.

6. An antimicrobial particle as claimed in claim 1 comprising 0.1 to 5% terpineol and 0.1 to 10% thymol by weight of the particle.

7. An antimicrobial particle as claimed in claim 1 comprising 1 to 19% coating material by weight of the particle.

8. A composition for care or cleansing of the external surface of a human or animal body or the external surface of an inanimate object, said composition comprising 0.5 to 20% of an antimicrobial particle as claimed in claim 1 by weight of the composition.

9. A composition as claimed in claim 8 wherein the external surface of the human body includes skin, hair, scalp, the axilia or the oral cavity.

10. A composition as claimed in claim 8 comprising 1 to 80% surfactant by weight of the composition.

11. A method of disinfecting a surface comprising the steps of:
   (a) applying a composition as claimed in claim 8 on to the surface; and
   (b) rinsing the surface with a suitable solvent.

* * * * *